(12) United States Patent
Fales

(10) Patent No.: US 9,823,332 B2
(45) Date of Patent: Nov. 21, 2017

(54) POSITION LOCATION AIDED BY CHEMICAL CHARACTERISTIC

(71) Applicant: QUALCOMM Incorporated, San Diego, CA (US)

(72) Inventor: Mary A. Fales, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 805 days.

(21) Appl. No.: 13/645,278

(22) Filed: Oct. 4, 2012

(65) Prior Publication Data
US 2014/0100793 A1    Apr. 10, 2014

(51) Int. Cl.
| | | |
|---|---|---|
| G06F 19/00 | (2011.01) | |
| G01S 5/00 | (2006.01) | |
| G01S 19/25 | (2010.01) | |
| G01S 19/42 | (2010.01) | |
| G01N 33/00 | (2006.01) | |

(52) U.S. Cl.
CPC ............ *G01S 5/00* (2013.01); *G01N 33/0009* (2013.01); *G01S 19/25* (2013.01); *G01S 19/42* (2013.01)

(58) Field of Classification Search
None
See application file for complete search history.

(56) References Cited

U.S. PATENT DOCUMENTS

| | | | | |
|---|---|---|---|---|
| 6,323,807 B1 * | 11/2001 | Golding | ................. | G01C 21/20 342/419 |
| 7,218,938 B1 * | 5/2007 | Lau | ....................... | G01C 21/00 340/539.13 |
| 7,848,765 B2 | 12/2010 | Phillips et al. | | |
| 8,035,508 B2 | 10/2011 | Breed | | |
| 8,086,266 B2 | 12/2011 | Kotidis | | |
| 8,174,931 B2 * | 5/2012 | Vartanian et al. | .............. | 367/99 |

(Continued)

FOREIGN PATENT DOCUMENTS

EP    2278357 A2    1/2011

OTHER PUBLICATIONS

Walker, Denise, Mass Notification and Crisis Communications: Planning, Preparedness, and Systems (CRC Press; Pub. Date: Dec. 19, 2011).*

(Continued)

*Primary Examiner* — Paul D Lee
*Assistant Examiner* — Mark Crohn
(74) *Attorney, Agent, or Firm* — Thien T. Nguyen

(57) ABSTRACT

A mobile device includes a chemical sensor to detect chemicals in the environment in which the mobile device is present. The detected chemicals are analyzed and used to generate a chemical characteristic of the environment. The chemical characteristic of the environment is used to determine location related data for the mobile device. For example, an implemented within or remote chemical characteristic database that stores chemical characteristics associated with location related data may be searched based on the chemical characteristic of the environment to determine the location of the mobile device. The location related data may be a location of the mobile device or assistance data that may be used to assist in generating a more accurate position fix, e.g., using a satellite positioning system. The location related data may simply whether the mobile device is inside or outside or the floor of a multi-floor building.

50 Claims, 3 Drawing Sheets

(56) References Cited

U.S. PATENT DOCUMENTS

| | | | |
|---|---|---|---|
| 2004/0027243 A1 | 2/2004 | Carrender | |
| 2004/0119591 A1* | 6/2004 | Peeters | 340/539.26 |
| 2005/0101250 A1 | 5/2005 | Helal et al. | |
| 2006/0279732 A1 | 12/2006 | Wang et al. | |
| 2008/0169921 A1 | 7/2008 | Peeters | |
| 2013/0079033 A1* | 3/2013 | Gupta | H04W 64/00 |
| | | | 455/456.2 |

OTHER PUBLICATIONS

Andres R., et al.,"Nanoscale Science and Technology for the Development of Environmental Sensors", Grant # DE-FG02-01ER15207, Final Report, Jan. 2007, 15 Pages.

Argonne National Laboratory, "Chemical Agent Detection and Identification System", Homeland Security, The University of Chicago, 2002, 2 Pages.

Jo W.K., et al., "Comparison of outdoor and indoor mobile source-related volatile organic compounds between low- and high-floor apartments", Environ Res., Jun. 2003, vol. 92 (2), pp. 166-171.

Zhang X.Y., et al.,"Atmospheric aerosol compositions in China: spatial/temporal variability, chemical signature, regional haze distribution and comparisons with global aerosols", Atmospheric Chemistry and Physics, 2012, vol. 12, pp. 779-799.

International Search Report and Written Opinion—PCT/US2013/056651—ISA/EPO—dated Nov. 19. 2013.

* cited by examiner

POSITION LOCATION AIDED BY CHEMICAL CHARACTERISTIC

BACKGROUND

Background Field

Embodiments of the subject matter described herein are related generally to determining a position for a mobile device, and more specifically for determining a position of a mobile device based on detected chemicals in the environment.

Relevant Background

Obtaining accurate position information for mobile devices, such as cellular telephones or other wireless communication devices, is becoming prevalent in the communications industry. A common means to determine the location of a device is to use a satellite position system (SPS), such as the well-known Global Positioning Satellite (GPS) system or Global Navigation Satellite System (GNSS), which employ a number of satellites that are in orbit around the Earth. One limitation of current SPS systems is that their operation is limited to situations in which multiple satellites are clearly in view, without obstructions. For example, obtaining a traditional SPS position fix while inside a building is typically difficult, if not impossible. Thus, once inside a building, a terrestrial positioning technique will be used. Terrestrial positioning techniques rely on data from non-SPS sources, such as wireless signals obtained from a wireless local area network (WLAN) or WiFi, or vision based techniques.

Obtaining a position fix using a traditional SPS system or terrestrial navigation techniques, however, may be time consuming and may drain battery power. For example, when a mobile device moves between indoors and outdoors, the mobile device may try to use an inappropriate or unnecessary positioning technique (e.g., SPS while indoors) for a period of time before changing to a different appropriate positioning technique. Thus, there may be a delay in determining an accurate position using the most appropriate technique. Hysteresis in the time for the mobile device to accurately determine when to switch between the indoor navigation mode and outdoor navigation mode is present as the threshold for determining which mode to use is not always clear. For example, a WLAN can broadcast several hundreds of meters. Accordingly, a mobile device may determine incorrectly that it is inside a building based on a received WLAN signal, when the mobile device is outside but relatively near the building. This uncertainty period can cause a delay in obtaining an accurate position fix using the appropriate location technique. Moreover, the mobile device will run both the indoor and outdoor systems in order to determine when to switch between the two positioning modes. Running systems for both modes, however, quickly drains battery life. Thus, reducing the transition time between modes is desirable.

Additionally, as is well known, an SPS positioning system requires that the mobile device lock on to the signals from a number, e.g., at least four, satellites. Thus, if the mobile device is moved a significant distance while the SPS positioning system is turned off, e.g., when a user travels on an airline to another city, a cold start may be required. A cold start may take considerable time, as long as twelve minutes, because the receiver must search for a satellite lock by running through all of the codes and frequency combinations until it locks on a satellite. To avoid cold starts, some mobile devices have the capability to download the current almanac and ephemeris data from a network to save acquisition time. This is called assisted GPS (A-GPS). However, some devices are still stand alone GPS devices. For standalone devices, it is desirable to have an approximate position fix so that the device can lock onto satellites and obtain an accurate position fix more quickly than if using a cold start. Additionally, assisted GPS mobile devices may not have network services in other countries. Thus, there may be situations where even an A-GPS device may be forced to perform an undesirable cold start. Thus, improvements for position determination of mobile devices are desired.

SUMMARY

A mobile device includes a chemical sensor to detect chemicals in the environment in which the mobile device is present. The detected chemicals are analyzed and used to generate a chemical characteristic of the environment. The chemical characteristic of the environment is used to determine location related data for the mobile device. For example, an implemented within or remote chemical characteristic database that stores chemical characteristics associated with location related data may be searched based on the chemical characteristic of the environment to determine the location of the mobile device. The location related data may be a location of the mobile device or assistance data that may be used to assist in generating a more accurate position fix, e.g., using a satellite positioning system. The location related data may simply whether the mobile device is inside or outside or the floor of a multi-floor building.

In one aspect, a method includes using a chemical sensor in a mobile device to detect chemicals in an environment in which the mobile device is present; analyzing chemicals detected by the chemical sensor to determine a chemical characteristic of the environment; and determining location related data for the mobile device using the chemical characteristic of the environment.

In one aspect, a mobile device includes a chemical sensor that detects chemicals in an environment in which the mobile device is present; and a processor coupled to the chemical sensor, the processor receives data from the chemical sensor in response the detected chemicals, the processor configured to analyze the data from the chemical sensor to determine a chemical characteristic of the environment and use the chemical characteristic to determine location related data for the mobile device.

In one aspect, a mobile device includes means for detecting chemicals in an environment in which the mobile device is present; means for analyzing detected chemicals to determine a chemical characteristic of the environment; and means for determining location related data for the mobile device using the chemical characteristic of the environment.

In one aspect, a non-transitory computer-readable medium including program code stored thereon includes program code to use a chemical sensor to detect chemicals in an environment in which a mobile device is present; program code to analyze the chemicals detected by the chemical sensor to determine a chemical characteristic of the environment; and program code to determine location related data for the mobile device using the chemical characteristic of the environment.

In one aspect, a method includes receiving data from a remote mobile device related to a chemical characteristic of an environment in which the remote mobile device is present; determining location related data for the remote mobile device based on the chemical characteristic; and transmitting the location related data to the remote mobile device.

In one aspect, an apparatus includes an external interface for communicating with a remote mobile device; and a processor coupled to the external interface to receive data related to a chemical characteristic of an environment in which the remote mobile device is present, the processor being configured to determine location related data for the remote mobile device based on the chemical characteristic; and to cause the external interface to transmit the location related data to the remote mobile device.

In one aspect, an apparatus includes means for receiving data from a remote mobile device related to a chemical characteristic of an environment in which the remote mobile device is present; means for determining location related data for the remote mobile device based on the chemical characteristic; and means for transmitting the location related data to the remote mobile device.

In one aspect, a non-transitory computer-readable medium including program code stored thereon, includes program code to receive data from a remote mobile device related to a chemical characteristic of an environment in which the remote mobile device is present; program code to determine location related data for the remote mobile device based on the chemical characteristic; and program code to transmit the location related data to the remote mobile device.

DETAILED DESCRIPTION

Figure 1:
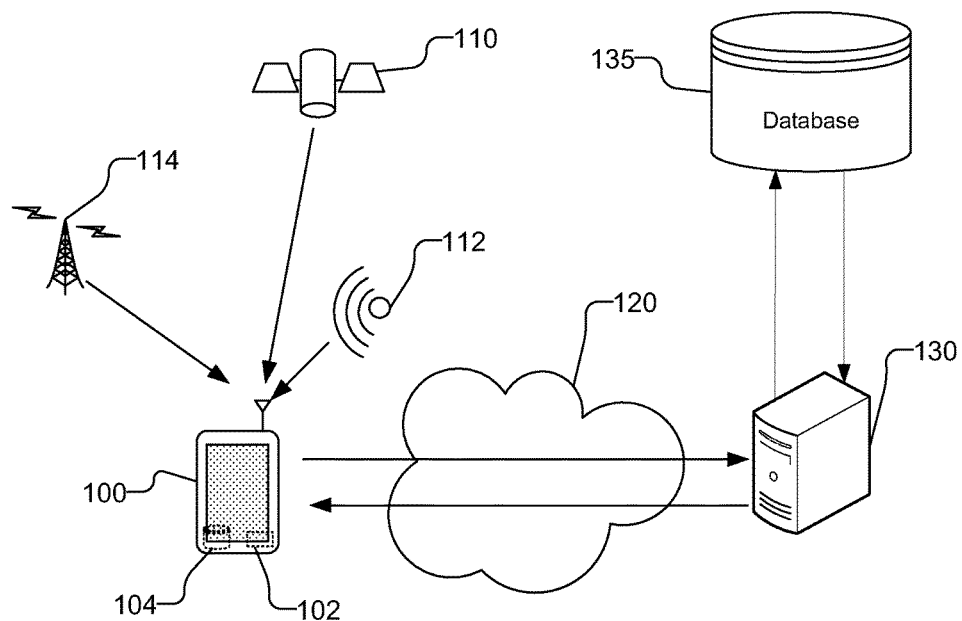
FIG. 1 illustrates a block diagram showing a system in which detected chemicals in the environment, e.g., in the form of a chemical characteristic, is used to assist in determining the location of a mobile device.

FIG. 1 illustrates a block diagram showing a system in which detected chemicals in the environment, e.g., in the form of a chemical characteristic, are used to assist in determining the location of a mobile device 100. As illustrated, the mobile device 100 includes a chemical sensor 102 that is used to detect chemicals in the environment in which the mobile device 100 is present. The detected chemicals may be used to generate a chemical characteristic of the environment. The determined chemical characteristic may be a unique or semi-unique chemical signature that can be used to identify the location of the mobile device 100, e.g., using a database 104 that may be stored on the mobile device 100 or using a remote database 135 via network 120 and remote server 130. The remote database 135 may store chemical characteristics that are associated with different locations, which may be crowdsourced in a continuous or periodic fashion. The on-board database 104 similarly store chemical characteristics that are associated with different locations, which may be downloaded from the remote database 135 and/or generated based on measurements of from the mobile device 100.

As used herein, a mobile device (MS) refers to a device such as a cellular or other wireless communication device, personal communication system (PCS) device, personal navigation device (PND), Personal Information Manager (PIM), Personal Digital Assistant (PDA), laptop or other suitable mobile device which is capable of receiving wireless communication and/or navigation signals, such as navigation positioning signals. The term "mobile device" is also intended to include devices which communicate with a personal navigation device (PND), such as by short-range wireless, infrared, wireline connection, or other connection—regardless of whether satellite signal reception, assistance data reception, and/or position-related processing occurs at the device or at the PND. Also, "mobile device" is intended to include all devices, including wireless communication devices, computers, laptops, etc. which are capable of communication with a server, such as via the Internet, WiFi, or other network, and regardless of whether satellite signal reception, assistance data reception, and/or position-related processing occurs at the device, at a server, or at another device associated with the network. Any operable combination of the above are also considered a "mobile device."

The chemical sensor 102 may be a ChemFET, ChemDiode, sometimes referred to as a Nano-nose, or the like, which are well known to those skilled in the art. Chemical sensors may have a single sensor element or a plurality of sensor elements, e.g., several thousand elements, on a single chip. For example, a ChemDiode sensor may be a square micron in area, but may contain approximately 40,000 molecule/nanoparticle/sensor elements. Both ChemDiodes and ChemFETs operate in a manner similar to traditional field effect transistors (FETs) and diodes, but use a chemical that binds to the gate (or provides the forward bias for a diode) to turn the device on. Chemical sensors may be manufactured to respond to certain types of chemicals. For example, a ChemFETs can be manufactured to turn on the (gate) when certain levels of formaldehyde are present.

The resulting signals from the chemical sensors may be coupled to and analyzed using an on-board processor in the mobile device 100 to determine a chemical characteristic of the environment. The chemical characteristic may a unique chemical signature for the location or may be semi-unique, but useful in identifying locations frequented by the user. Thus, using the chemical characteristic an approximate or a specific location of the mobile device may be determined.

By way of example, unique chemical signatures may be determined for major cities. Thus, the mobile device 100 may detect and measure several types of chemicals in the environment with the chemical sensor 102 and compare the measured chemicals to the chemical signatures for different cities, e.g., stored in remote database 135, the on-board database 104, or in memory 105$m$, shown in FIG. 3. By way of example, the chemical signatures of cities or regions may be periodically crowdsourced and stored in the remote database 135, and/or downloaded to the on-board database 104 in the mobile device 100. The mobile device 100 may thus measure the chemical characteristic of the environment with the chemical sensor 102 and determine an approximate location with an accuracy that is at the city level or possibly smaller regions, such as specific neighborhoods in a city. Moreover, even if the accuracy is at a city level or even larger geographic region level, the determined approximate location may be adequate to assist in determining a more accurate position fix from an SPS system 110. Thus, the based on the measured chemical characteristic of the environment, location related data, which may be, e.g., a general or specific location of the mobile device or assistance data that may be used to assist in generating a more accurate position fix, e.g., using a satellite positioning system. The SPS system 110 is a system of transmitters positioned to enable entities to determine their location on or above the Earth based, at least in part, on signals received from the transmitters. In a particular example, such transmitters may be located on Earth orbiting satellite vehicles (SVs), e.g., in a constellation of Global Navigation Satellite System (GNSS) such as Global Positioning System (GPS), Galileo, Glonass or Compass or other non-global systems. Thus, as used herein an SPS may include any combination of one or more global and/or regional navigation satellite systems and/or augmentation systems, and SPS signals may include SPS, SPS-like, and/or other signals associated with such one or more SPS. The detected chemical characteristic of the environment may be used, e.g., to provide an approximate location of the mobile device 100 to assist in a cold start. In other words, based on the approximately location of the mobile device 100, the SVs that should be visible to the mobile device 100 can be quickly determined thereby reducing the search for SVs that is required in a cold start. For example, the mobile device 100 may estimate what SV's to look for based on the old almanac and ephemeris data and the known approximate location determined from the chemical signature. This solution would be useful to a standalone GPS device that cannot obtain assisted data from a network. This solution may also be useful to an assisted GPS device, for example, if the device has traveled to another geographical location in which it has no network services currently available.

Additionally, the determined approximate location of the mobile device 100 may be simply whether the mobile device is inside or outside a building. For example, certain common chemicals, e.g., formaldehyde, are typically present in the air where building materials are used, i.e., inside buildings. The chemical sensor 102 may be configured to detect only a single relevant chemical (e.g., formaldehyde) or a small number of chemicals, rather than thousands of chemicals, from which a determination of the approximate location of the mobile device 100, e.g., indoors or outdoors, may be made. Thus, by detecting a chemical characteristic that includes a limited number of chemicals, the mobile device 100 may determine whether the device is inside or outside. The mobile device 100 may compare the chemical characteristic detected by the chemical sensor 102 to an on-board database 104 or remote database 135 to determine if the mobile device 100 is likely inside or outside. Alternatively, the mobile device 100 may simply compare a currently detected chemical characteristic to a threshold characteristic to determine if the mobile device 100 is likely inside or outside. The mobile device 100 may alternatively compare a currently detected chemical characteristic to a previously detected chemical characteristic to determine if a sufficiently large change has occurred, e.g., compared to a threshold, indicating that the mobile device 100 has moved from an indoor environment to an outdoor environment or vice versa. With knowledge that the mobile device 100 is inside a building, for example, the mobile device 100 may eliminate SPS positioning as a possible positioning technique and instead may use wireless signals, e.g., from an access point 112 or cellular base station 114, to determine a position. The indoor v. outdoor determination time may be reduced using these techniques, and thus help save the mobile device 100 battery power. These techniques may also help reduce the time of uncertainty in the mobile device 100 location, thereby providing an accurate location to a user more quickly. Alternatively, when the mobile device 100 determines that it is located outside based on the detected chemical characteristic of the environment, the mobile device 100 may use SPS system 110, an A-GPS system, or a hybrid SPS system, which uses SPS data with terrestrial signals to determine a position. Thus, an accurate position fix may be acquired quickly while minimizing location uncertainty and drainage of the battery due to the use of an inappropriate or unnecessary positioning technique.

In another example, the approximately location of the mobile device 100 may be determined as a specific floor of a building, e.g., if different floors of a building have different chemical characteristics. For example, the levels of volatile organic compounds (VOCs) or other such chemicals may vary in multistory buildings with respect to height. Thus, by measuring such a chemical characteristic with the chemical sensor 102, the mobile device 100 may be able to determine a specific or approximate floor where the device is located, e.g., based on-board database 104 or remote database 135. In addition, these techniques may assist the mobile device in determining its presence at any location that can be distinguished by chemical signature. For example, the mobile device may be able to determine which room of a home the device is in, which terminal of an airport it is in, if the device is in a particular vehicle, etc.

Therefore, the location of the mobile device 100 may be acquired with an accuracy that is sufficient that no other positioning techniques are necessary. For example, a user's office may have a unique semi-unique chemical signature, which can be detected by the mobile device 100 and stored in the on-board database 104. Future detection of the same chemical signature may then be used to quickly identify the location of the mobile device 100. An on-board database may be built or refined based on user feedback and confirmation. For example, a user may respond to a prompt by the mobile device asking to confirm a guessed location. Once that feedback is received, the location with the associated chemical signature (CHEM_LOC parameter) can be stored in the on-board database for future use.

A mobile device may build a database based on measuring its location with, for example, A-GPS methods and measure its chemical signature at that location and time, and then store the associated chemical signature with location data (CHEM_LOC parameters). This data can be stored on-board the mobile device 100 or with a remote server 130. In this aspect, the chemical signature or the location event may trigger the need to measure and store the associated parameters. In other words, the mobile device may be set up to periodically measure the chemical signatures, and upon this event, the device may then want to obtain an A-GPS position fix. Alternatively, a change in the chemical environment based on a threshold level, may trigger the mobile device to then measure the location and associate it with the chemical signature. Many different case uses can be visualized in light of the present disclosure.

Even if the chemical characteristic of a location is not unique, the chemical characteristic may be sufficiently unique with respect to locations frequented by the user that the detected chemical characteristic can be used to determine an accurate location of the mobile device.

The determination of the chemical characteristics for different locations may be based on crowd sourcing, e.g., using multiple mobile devices with chemical sensors, or based on stationary sensors that are present in the different locations. Thus, for example, mobile devices equipped with chemical sensors may record and upload the chemical characteristics and location to the remote server 130, which may average, analyze the data and update the remote database 135. Additionally, the mobile device 100 may create the on-board database 104. For example, a feedback or training application may be used, in which the mobile device 100 to manually identify a location when unique or semi-unique chemical characteristics are detected. Chemical characteristics may change over time, e.g., due to changes in the weather, prevailing winds, seasons, etc., and thus, it may be desirable to frequently update the chemical characteristic databases 104 and 135. The identified location and associated chemical characteristic are stored in database 104 (and if desired uploaded to remote database 135) so that in the future when the chemical sensor 102 registers the same (or nearly the same within a threshold) chemical characteristic, the location of the mobile device can be quickly identified without requiring a traditional position fix, thereby reducing battery consumption. If desired, if the chemical characteristic is not "unique" the location may be provided based on probability.

Additionally, the chemical characteristic and determined location may be used in applications such as Geofencing. For example, the detection of movement of the mobile device 100 from one city to another based on the detected chemical characteristics may be used to trigger specific applications, including obtaining a position fix, i.e., an accurate position determination. Further, the chemical sensor 102 may be used to track movement of people or pets from an area that has a known chemical signature, e.g., based on a threshold or window value. For example, if the detected chemical signature changes by a sufficient amount, it is likely that the mobile device has moved outside the geofence, thereby triggering a position fix request. Accordingly, the number of required position fixes is reduced thereby saving battery power.

Figure 2A:
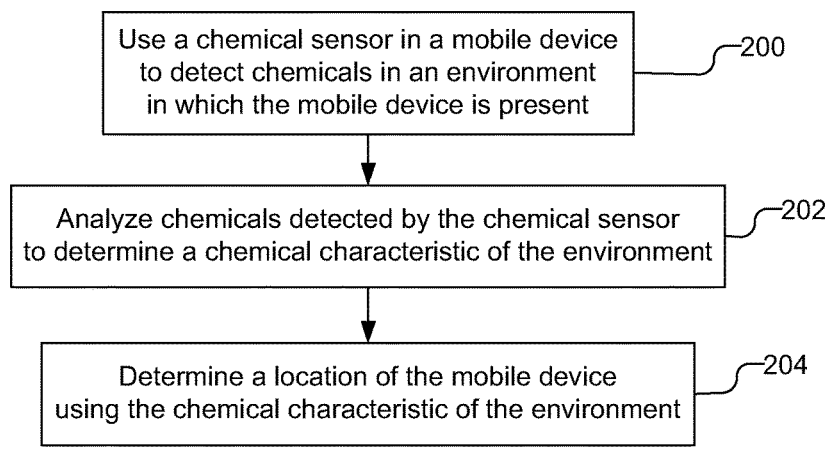
FIG. 2A is a flow chart illustrating a method of using a detected chemical characteristic of an environment to assist in the determination of the location of a mobile device.

FIG. 2A is a flow chart illustrating a method of using a detected chemical characteristic of an environment to assist in the determination of the location of a mobile device. As illustrated, the mobile device uses a chemical sensor to detect chemicals in an environment in which the mobile device is present (200). The chemicals detected by the chemical sensor are analyzed to determine a chemical characteristic of the environment (202). The chemical characteristic of the environment is used to determine location related data for the mobile device (204). For example, the location related data for the mobile device thus may be a location for the mobile device or assistance data for the remote mobile device to determine its location. The chemical characteristic of the environment may be a unique chemical signature. The location related data for the mobile device may be determined by transmitting the chemical characteristic to remote server 130 and receiving the location related data for the mobile device from the remote server 130. Alternatively, the location related data for the mobile device may be determined by searching a chemical characteristic database 104 for the location related data for with the chemical characteristic of the environment. A database may be built by way of receiving chemical signature data associated with known or accurate location related data from more than one mobile device 100, or the same mobile device at different times. For example, a mobile device 100 may be downtown in a city, and have an accurate position fix for the location based on known positioning techniques. The mobile device 100 may measure the current chemical signature at the location and associates this data with the known position. The chemical signature data and associated location related data may be stored in memory on the mobile or sent to a server. This associated data could collectively be called a Chem_LOC parameter. A server or local processor could collect and statistically represent all of the Chem_LOC parameters from various mobile devices. It could also collect the CHEM_LOC parameters from the same mobile device over time. Thus, a time stamp and/or mobile ID may be desirable to attach to the CHEM_LOC parameter. Thus, a known physical location may have a range of valid chemical signatures that would determine that location or geographical area. Thus, for example, the location of the mobile device may be determined by determining a location related data, such as an approximate position of the mobile device or assistance data, using the characteristics of the environment and using the location related data to assist in producing a position fix for the mobile device. The location related data for the mobile device may be determined by determining whether the mobile device is inside or outside of a building or by determining a floor of a building that the mobile device is on. Additionally, the characteristic of the environment may be used for geofencing, e.g., based on the determined location of the mobile device.

Figure 2B:
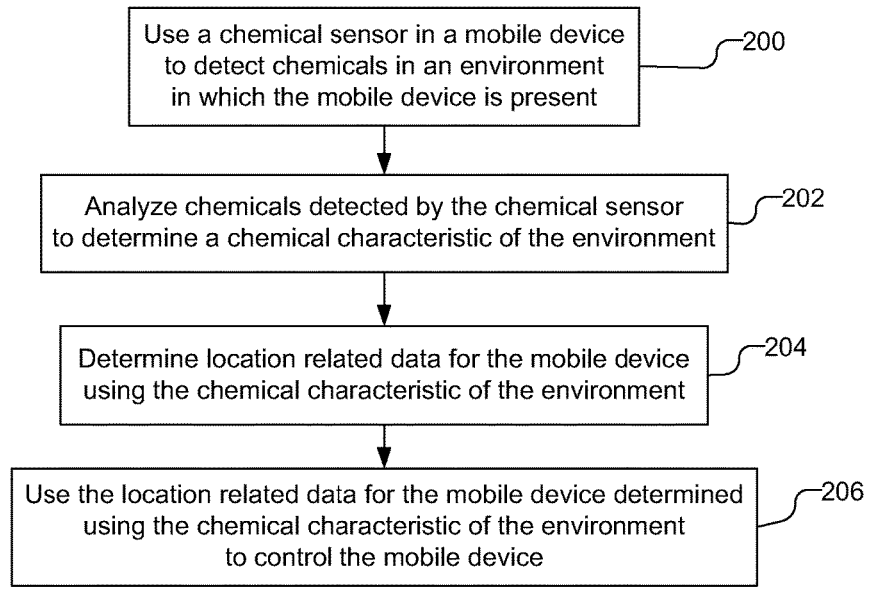
FIG. 2B is another flow chart illustrating a method of using a detected chemical characteristic of an environment to assist in the determination of the location of a mobile device.

FIG. 2B is a flowchart similar to the flowchart shown in FIG. 2A, like designated elements being the same. As illustrated in FIG. 2B, however, the location related data for the mobile device determined using the chemical characteristic of the environment may be used to control the mobile device (206). In one implementation, the location related data determined based on the chemical characteristic of the environment may be used to control the position determination performance of the mobile device. For example, the mobile device may be controlled to switch from a first position determination mode, e.g., an SPS mode, to a second position determination mode, e.g., a terrestrial positioning technique, using signals from a WLAN, WiFi, cellular signals, dead-reckoning, vision based techniques, etc., or vice-versa, based on the location related data for the mobile device determined using the chemical signature of the environment. Thus, the mobile device may switch between an indoor position determination technique and an outdoor position determination technique based on whether the mobile device is determined to be inside or outside of a building based on the chemical signature of the environment. In another example, the mobile device may be controlled to determine whether a position fix, as provided by an SPS system or the like, is required based on the location related data for the mobile device determined using the chemical signature of the environment.

In addition, a processor may be used to help analyze and manage false environmental triggers. For example, if the mobile device is placed inside a purse, a change in the chemical environment may be falsely triggered. The mobile device may determine incorrectly that it is inside a building rather than outdoors inside a purse. The processor may have levels of certainty associated with chemical signature changes based on the degree of chemical changes detected, the types of chemicals detected, and the transition times of the chemical changes. These parameters may be used to help determine the accuracy of an environment change.

A mobile device 100 may measure the chemical signature of its environment periodically, or based on other criteria, such as time of day. It may also be capable of doing a preliminary rough chemical signature measurement and analysis prior to performing a full chemical signature measurement and analysis, which may help saver battery power if the full chemical signature analysis is unnecessary.

Figure 3:
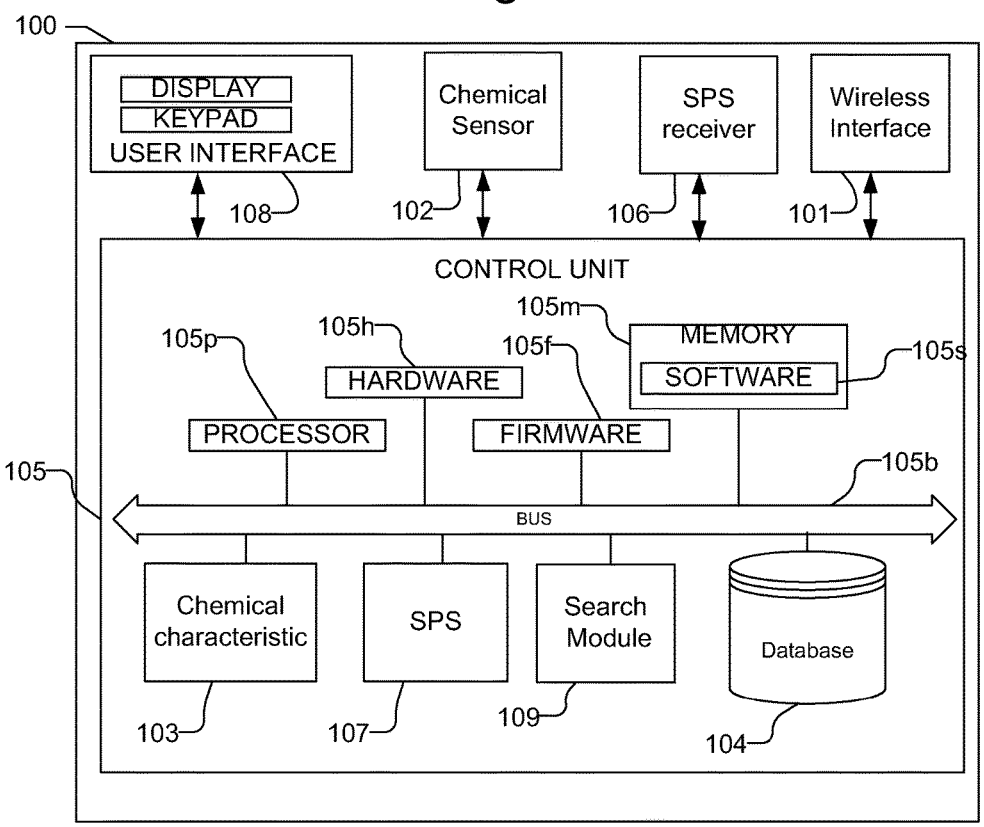
FIG. 3 is a block diagram of a mobile device capable of detecting a chemical characteristic of an environment to assist in the determination of the location of the mobile device.

FIG. 3 is a block diagram of a mobile device 100 capable of detecting a chemical characteristic of an environment to assist in the determination of the location related data for the mobile device. The mobile device 100 includes a chemical sensor 102, which may be a discrete sensor or an array of sensors. The chemical sensor 102 may be, e.g., a ChemFET, ChemDiode, Nano-nose, or the like. Moreover, the chemical sensor 102 may include a single sensor element to detect a specific chemical characteristic or a plurality of elements to detect a chemical pattern. The mobile device 100 may additionally be coupled to a wireless interface 101 that may be used to communicate with the remote server 130, e.g., to transmit a chemical characteristic to the remote server 130, which searches remote database 135 and in response returns a location related data associated with the chemical characteristic.

The wireless interface 101 may be used in any various wireless communication networks such as a wireless wide area network (WWAN), a wireless local area network (WLAN), a wireless personal area network (WPAN), and so on. The term "network" and "system" are often used interchangeably. A WWAN may be a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, Long Term Evolution (LTE), and so on. A CDMA network may implement one or more radio access technologies (RATs) such as cdma2000, Wideband-CDMA (W-CDMA), and so on. Cdma2000 includes IS-95, IS-2000, and IS-856 standards. A TDMA network may implement Global System for Mobile Communications (GSM), Digital Advanced Mobile Phone System (D-AMPS), or some other RAT. GSM and W-CDMA are described in documents from a consortium named "3rd Generation Partnership Project" (3GPP). Cdma2000 is described in documents from a consortium named "3rd Generation Partnership Project 2" (3GPP2). 3GPP and 3GPP2 documents are publicly available. A WLAN may be an IEEE 802.11x network, and a WPAN may be a Bluetooth® network, an IEEE 802.15x, or some other type of network. Moreover, any combination of WWAN, WLAN and/or WPAN may be used.

The mobile device 100 may further include an SPS receiver 106 for receiving position data from SPS system 110, which may be used to determine a position fix of the mobile device 100, as discussed above. The mobile device may be, e.g., an A-GPS device or a standalone GPS device. The mobile device 100 may further include a user interface 108 that may include e.g., a display, as well as a keypad or other input device through which the user can input information into the mobile device 100.

The mobile device 100 also includes a control unit 105 that is connected to and communicates with the chemical sensor 102, wireless interface 101 and SPS receiver 106. The control unit 105 receives and processes data obtained from chemical sensor 102 to generate a chemical characteristic. The control unit 105 additionally receives and processes data from the wireless interface 101 and SPS receiver 106 and may control the wireless interface 101 to transmit the chemical sensor data or the detected chemical characteristic to the remote server 130. The control unit 105 may be provided by a bus 105$b$, processor 105$p$ and associated memory 105$m$, hardware 105$h$, firmware 105$f$, and software 105$s$. The control unit 105 is further illustrated as including chemical characteristic module 103 that receives the data from chemical sensor 102 and generates a chemical characteristic in response. The control unit 105 is also illustrated as including a search module 109 and the database 104, which stores chemical characteristics associated with location related data, and is searched by the search module 109 and returns location related data based on the chemical characteristic generated by chemical characteristic module 103. The control unit 105 may include an SPS module 107 that receives data from the SPS receiver 106 to determine a position fix. The SPS module 107 may use the location related data returned from the database 104 to narrow the search for visible SVs when initiating a position fix, e.g., from a cold start.

The chemical characteristic module 103 and SPS module 107 are illustrated separately from processor 105$p$ for clarity, but may be part of the processor 105$p$ or implemented in the processor based on instructions in the software 105$s$ which is run in the processor 105$p$. It will be understood as used herein that the processor 105$p$ can, but need not necessarily include, one or more microprocessors, embedded processors, controllers, application specific integrated circuits (ASICs), digital signal processors (DSPs), and the like. The term processor is intended to describe the functions implemented by the system rather than specific hardware. Moreover, as used herein the term "memory" refers to any type of computer storage medium, including long term, short term, or other memory associated with the mobile device, and is not to be limited to any particular type of memory or number of memories, or type of media upon which memory is stored.

The methodologies described herein may be implemented by various means depending upon the application. For example, these methodologies may be implemented in hardware 105$h$, firmware 113$f$, software 105$s$, or any combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in memory 105$m$ and executed by the processor 105$p$. Memory 105$m$ may be implemented within or external to the processor 105$p$. If implemented in firmware and/or software, the functions may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Thus, the mobile device 100 includes a means for detecting chemicals in an environment in which the mobile device is present, which may be the chemical sensor 102, which may be, e.g., a ChemFET, ChemDiode, Nano-nose, or the like. A means for analyzing detected chemicals to determine a chemical characteristic of the environment may be, e.g., the chemical characteristic module 103 and/or processor 105$p$ using program code stored in memory 105$m$. A means for determining location related data for the mobile device using the chemical characteristic of the environment may include, e.g., the search module 109, the chemical characteristic database 104 and processor 105$p$ using program code stored in memory 105$m$, or the wireless interface 101 that is used transmit the chemical characteristic to a remote server 130 coupled to the remote chemical characteristic database 135 and receive the location related data for the mobile device in response. A means for using the chemical characteristic of the environment for geofencing may be, e.g., the processor 105$p$ using program code stored in memory 105$m$.

Figure 4:
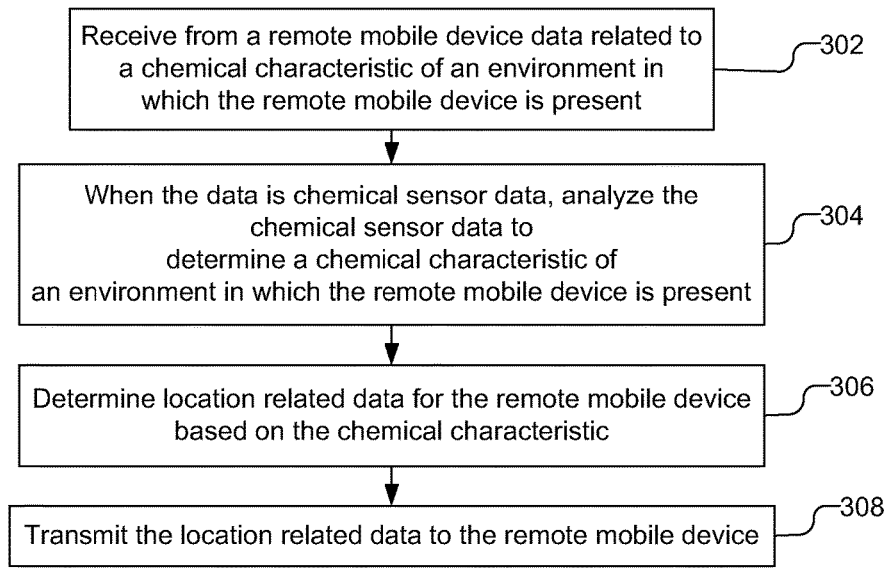
FIG. 4 is a flow chart illustrating a method performed by server for using a detected chemical characteristic of an environment to assist in the determination of the location of a mobile device.

FIG. 4 is a flow chart illustrating a method performed by server 130 for using a detected chemical characteristic of an environment to assist in the determination of the location of a mobile device. As illustrated, the server 130 receives from a remote mobile device data related to a chemical characteristic of an environment in which the remote mobile device is present (302). By way of example, the data related to the chemical characteristic may be the chemical characteristic itself, determined by the mobile device 100. Alternatively, the data related to the chemical characteristic may be chemical sensor data provided by the remote mobile device, and thus, the server 130 analyzes the chemical sensor data to determine a chemical characteristic of an environment in which the remote mobile device is present (304), which may be performed as discussed above. Location related data for the remote mobile device is determined based on the chemical characteristic (306), as discussed above. For example, the server 130 may search the chemical characteristic database 135 for the location related data associated with the chemical characteristic of the environment. The location related data may be, e.g., the location of the mobile device or assistance data that may be used by the mobile device to determine its own location, e.g., using a satellite positioning system. The location related data may be transmitted to the remote mobile device (308).

Figure 5:
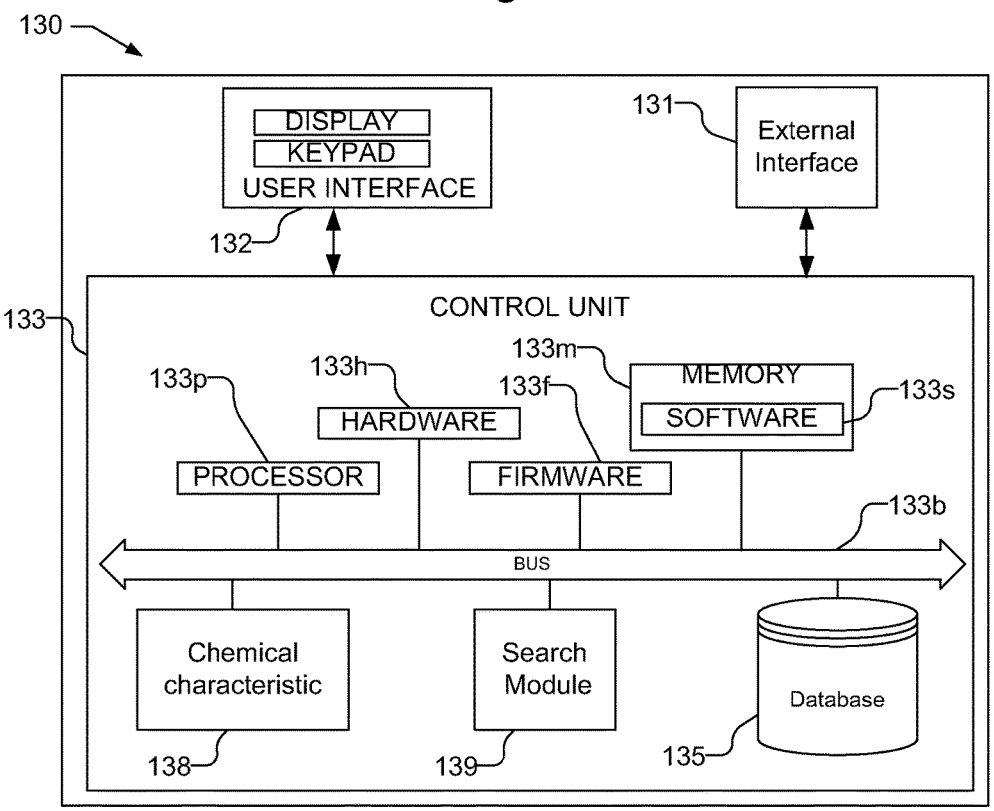
FIG. 5 is a block diagram of the server capable of determining a location of the remote mobile device based on the chemical sensor data provided by the remote mobile device.

FIG. 5 is a block diagram of the server 130 capable of determining location related data for the remote mobile device 100 based on the chemical sensor data provided by the remote mobile device. The server 130 includes an external interface 131 that is used to communicate with the mobile device 10 to receive the chemical sensor data, or the chemical characteristic if provided by the mobile device 100, and to transmit the determined location related data of the mobile device if desired. The server 130 may further include a user interface 132 that may include e.g., a display, as well as a keypad or other input device through which the user can input information into the server 130.

The external interface 131 may be a wired interface to a router (not shown) or a wireless interface used in any various wireless communication networks such as a wireless wide area network (WWAN), a wireless local area network (WLAN), a wireless personal area network (WPAN), and so on. The term "network" and "system" are often used interchangeably. A WWAN may be a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, Long Term Evolution (LTE), and so on. A CDMA network may implement one or more radio access technologies (RATS) such as cdma2000, Wideband-CDMA (W-CDMA), and so on. Cdma2000 includes IS-95, IS-2000, and IS-856 standards. A TDMA network may implement Global System for Mobile Communications (GSM), Digital Advanced Mobile Phone System (D-AMPS), or some other RAT. GSM and W-CDMA are described in documents from a consortium named "3rd Generation Partnership Project" (3GPP). Cdma2000 is described in documents from a consortium named "3rd Generation Partnership Project 2" (3GPP2). 3GPP and 3GPP2 documents are publicly available. A WLAN may be an IEEE 802.11x network, and a WPAN may be a Bluetooth® network, an IEEE 802.15x, or some other type of network. Moreover, any combination of WWAN, WLAN and/or WPAN may be used.

The server 130 also includes a control unit 133 that is connected to and communicates with the external interface 131. The control unit 133 accepts and processes the chemical sensor data (or chemical characteristic if provided) received from the mobile device. The control unit 133 may be provided by a bus 133$b$, processor 133$p$ and associated memory 133$m$, hardware 133$h$, firmware 133$f$, and software 133$s$. The control unit 133 is further illustrated as including a chemical characteristic module 138 that receives the chemical sensor data from the remote mobile device 100 via external interface 131, if provided, and generates a chemical characteristic in response. The control unit 133 is also illustrated as including a search module 139 and the database 135, which may be internal or external to the server 130, which stores chemical characteristics associated with location related data, e.g., locations or assistance data, and is searched by search module 139 and returns the location related data based on the chemical characteristic generated by chemical characteristic module 138 or provided by the remote mobile device 100 via the external interface 131.

The chemical characteristic module 138 and search module 139 are illustrated separately from processor 133$p$ for clarity, but may be part of the processor 133$p$ or implemented in the processor based on instructions in the software 133$s$ which is run in the processor 133$p$. Moreover, database 135 is illustrated as being within the control unit 133 and coupled directly to bus 133$b$, but may be external to the server 130 if desired.

It will be understood as used herein that the processor 133$p$ can, but need not necessarily include, one or more microprocessors, embedded processors, controllers, application specific integrated circuits (ASICs), digital signal processors (DSPs), and the like. The term processor is intended to describe the functions implemented by the system rather than specific hardware. Moreover, as used herein the term "memory" refers to any type of computer storage medium, including long term, short term, or other memory associated with the mobile device, and is not to be limited to any particular type of memory or number of memories, or type of media upon which memory is stored.

The methodologies described herein may be implemented by various means depending upon the application. For example, these methodologies may be implemented in hardware 133*h*, firmware 133*f*, software 133*s*, or any combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in memory 133*m* and executed by the processor 133*p*. Memory 133*m* may be implemented within or external to the processor 133*p*. If implemented in firmware and/or software, the functions may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Thus, the server 130 includes a means for receiving from a remote mobile device data related to a chemical characteristic of an environment in which the remote mobile device is present, which may be, e.g., the external interface 131. If the data related to the chemical characteristic of the environment comprises chemical sensor data, a means for analyzing the chemical sensor data to determine the chemical characteristic may be, e.g., the chemical characteristic module 138. Means for determining location related data for the remote mobile device based on the chemical characteristic may be, e.g., the search module 139, the chemical characteristic database 135*4* and processor 105*p* using program code stored in memory 105*m*. Means for transmitting the location related data to the remote mobile device may be, e.g., the external interface 131.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method comprising:
using a chemical sensor in a mobile device to detect chemicals in an environment in which the mobile device is present;
analyzing the chemicals detected by the chemical sensor to determine a chemical characteristic of the environment;
determining location related data for the mobile device based on the chemical characteristic of the environment and a database that stores chemical characteristics associated with location related data, wherein the location related data comprises a general or specific location of the mobile device or assistance data for the mobile device to determine its location; and
controlling the mobile device based on the location related data for the mobile device determined using the chemical characteristic of the environment, wherein controlling the mobile device comprises switching the mobile device between a first position determination technique using terrestrial wireless signals and a second position determination technique using a satellite positioning system based on whether the location related data indicates that the mobile device is inside of a building or outside of the building.

2. The method of claim 1, wherein determining the location related data for the mobile device using the chemical characteristic of the environment comprises transmitting the chemical characteristic to a remote server.

3. The method of claim 1, wherein determining the location related data for the mobile device using the chemical characteristic of the environment comprises receiving the location related data from a remote server.

4. The method of claim 1, wherein the database is implemented within the mobile device.

5. The method of claim 1, wherein controlling the mobile device further comprises determining whether a position fix is required based on the location related data for the mobile device determined using the chemical characteristic of the environment.

6. The method of claim 1, wherein the chemical characteristic of the environment is a unique chemical signature.

7. The method of claim 1, wherein determining the location related data for the mobile device comprises:
determining an approximate position of the mobile device using the chemical characteristic of the environment; and
using the approximate position to assist in producing a position fix for the mobile device.

8. The method of claim 1, wherein determining the location related data for the mobile device comprises determining whether the mobile device is inside or outside of the building.

9. The method of claim 8, wherein the first position determination technique comprises an indoor position determination technique used if the mobile device is inside the building and the second position determination technique comprises an outdoor position determination technique used if the mobile device is outside of the building.

10. The method of claim 1, wherein determining the location related data for the mobile device comprises determining a floor of a building that the mobile device is on.

11. The method of claim 1, further comprising using the chemical characteristic of the environment for geofencing.

12. A mobile device comprising:
a chemical sensor that detects chemicals in an environment in which the mobile device is present; and a processor coupled to the chemical sensor, the processor receives data from the chemical sensor, the processor configured to analyze the data from the chemical sensor to determine a chemical characteristic of the environment and use the chemical characteristic to determine location related data for the mobile device, based on the chemical characteristic of the environment and a database that stores chemical characteristics associated with location related data, wherein the location related data comprises a general or specific location of the mobile device or assistance data for the mobile device to determine its location; wherein the processor is configured to control a position determination for the mobile device based on the location related data for the mobile device determined using the chemical characteristic of the environment, wherein the processor is configured to control the position determination by being configured to switch the mobile device between a first position determination technique using terrestrial wireless signals and a second position determination technique using a satellite positioning system based on whether the location related data indicates that the remote mobile device is inside of a building and outside of the building.

13. The mobile device of claim 12, further comprising a wireless interface capable of transmitting and receiving wireless signals, wherein the processor is configured to use the chemical characteristic to determine the location related data for the mobile device by being configured to transmit the chemical characteristic to a remote server with the wireless interface.

14. The mobile device of claim 12, further comprising a wireless interface capable of transmitting and receiving wireless signals, wherein the processor is configured to use the chemical characteristic to determine the location related data for the mobile device by being configured to receive the location related data for the mobile device from a remote server with the wireless interface.

15. The mobile device of claim 12, wherein the processor is further configured to control the position determination by being configured to determine whether a position fix is required based on the location related data for the mobile device determined using the chemical characteristic of the environment.

16. The mobile device of claim 12, wherein the processor is configured to use the chemical characteristic to determine the location related data for the mobile device by being configured to search the database for the location related data associated with the chemical characteristic of the environment.

17. The mobile device of claim 12, wherein the chemical characteristic of the environment is a unique chemical signature.

18. The mobile device of claim 12, wherein the processor is configured to determine the location related data for the mobile device by being configured to determine an approximate position of the mobile device using the chemical characteristic of the environment, and use the approximate position to assist in producing a position fix for the mobile device.

19. The mobile device of claim 12, wherein the processor is configured to determine the location related data for the mobile device by being configured to determine whether the mobile device is inside or outside of the building.

20. The mobile device of claim 19, wherein the first position determination technique comprises an indoor position determination technique used if the mobile device is inside the building and the second position determination technique comprises an outdoor position determination technique used if the mobile device is outside of the building.

21. The mobile device of claim 12, wherein the processor is configured to determine the location related data for the mobile device by being configured to determine a floor of a building that the mobile device is on.

22. The mobile device of claim 12, wherein the processor is further configured to use the chemical characteristic of the environment for geofencing.

23. A mobile device comprising:
means for detecting chemicals in an environment in which the mobile device is present;
means for analyzing detected chemicals to determine a chemical characteristic of the environment;
means for determining location related data for the mobile device based on the chemical characteristic of the environment and a database that stores chemical characteristics associated with location related data, wherein the location related data comprises a general or specific location of the mobile device or assistance data for the mobile device to determine its location; and
means for controlling the mobile device based on the location related data for the mobile device determined using the chemical characteristic of the environment, wherein the means for controlling the mobile device comprises means for switching the mobile device between a first position determination technique using terrestrial wireless signals and a second position determination technique using a satellite positioning system based on whether the location related data indicates that the mobile device is inside of a building and outside of the building.

24. The mobile device of claim 23, wherein the means for determining the location related data for the mobile device using the chemical characteristic of the environment transmits the chemical characteristic to a remote server.

25. The mobile device of claim 23, wherein the means for determining the location related data for the mobile device using the chemical characteristic of the environment receives the location related data for the mobile device from a remote server.

26. The mobile device of claim 23, wherein the means for determining the location related data for the mobile device using the chemical characteristic of the environment searches the database for the location related data associated with the chemical characteristic of the environment.

27. The mobile device of claim 23, wherein the means for determining the location related data for the mobile device determines an approximate position of the mobile device using the chemical characteristic of the environment and uses the approximate position to assist in producing a position fix for the mobile device.

28. The mobile device of claim 23, wherein the means for determining the location related data for the mobile device determines whether the mobile device is inside or outside of a building or a floor of the building that the mobile device is on.

29. A non-transitory computer-readable medium including program code stored thereon, comprising:
program code to use a chemical sensor to detect chemicals in an environment in which a mobile device is present;
program code to analyze the chemicals detected by the chemical sensor to determine a chemical characteristic of the environment;
program code to determine a location related data for the mobile device based on the chemical characteristic of the environment and a database that stores chemical characteristics associated with location related data, wherein the location related data comprises a general or specific location of the mobile device or assistance data for the mobile device to determine its location; and program code to control the mobile device based on the location related data for the mobile device determined using the chemical characteristic of the environment, wherein the program code to control the mobile device comprises program code to switch the mobile device between a first position determination technique using terrestrial wireless signals and a second position determination technique using a satellite positioning system based on whether the location related data indicates that the remote mobile device is inside of a building and outside of the building.

30. The non-transitory computer-readable medium of claim 29, wherein the program code to determine the location related data for the mobile device using the chemical characteristic of the environment comprises program code to transmit the chemical characteristic to a remote server.

31. The non-transitory computer-readable medium of claim 29, wherein the program code to determine the location related data for the mobile device using the chemical characteristic of the environment comprises program code to receive the location related data for the mobile device from a remote server.

32. The non-transitory computer-readable medium of claim 29, wherein the program code to determine the location related data for the mobile device using the chemical characteristic of the environment comprises program code to search the database for the location related data associated with the chemical characteristic of the environment.

33. The non-transitory computer-readable medium of claim 29, wherein the program code to determine the location related data for the mobile device using the chemical characteristic of the environment comprises:
program code to determine an approximate position of the mobile device using the chemical characteristic of the environment; and
program code to use the approximate position to assist in producing a position fix for the mobile device.

34. The non-transitory computer-readable medium of claim 29, wherein the program code to determine the location related data for the mobile device determines whether the mobile device is inside or outside of a building or a floor of the building that the mobile device is on.

35. A method comprising:
receiving data from a remote mobile device related to a chemical characteristic of an environment in which the remote mobile device is present;
determining location related data for the remote mobile device based on the chemical characteristic and a database that stores chemical characteristics associated with location related data, wherein the location related data comprises a general or specific location of the remote mobile device or assistance data for the remote mobile device to determine its location;
transmitting the location related data to the remote mobile device; and
wherein the remote mobile device is controlled based on the location related data to switch the remote mobile device between a first position determination technique using terrestrial wireless signals and a second position determination technique using a satellite positioning system based on whether the location related data indicates that the remote mobile device is inside of a building and outside of the building.

36. The method of claim 35, wherein the data related to the chemical characteristic of the environment comprises chemical sensor data, the method further comprising analyzing the chemical sensor data to determine the chemical characteristic.

37. The method of claim 35, wherein the data related to the chemical characteristic of the environment comprises the chemical characteristic determined by the remote mobile device from chemical sensor data.

38. The method of claim 35, wherein determining the location related data for the remote mobile device based on the chemical characteristic comprises searching the database for the location related data associated with the chemical characteristic of the environment.

39. An apparatus comprising:
an external interface for communicating with a remote mobile device; and
a processor coupled to the external interface to receive data related to a chemical characteristic of an environment in which the remote mobile device is present, the processor being configured to determine location related data for the remote mobile device based on the chemical characteristic and a database that stores chemical characteristics associated with location related data, wherein the location related data comprises a general or specific location of the remote mobile device or assistance data for the remote mobile device to determine its location; and to cause the external interface to transmit the location related data to the remote mobile device, and wherein the remote mobile device is controlled based on the location related data to switch the remote mobile device between a first position determination technique using terrestrial wireless signals and a second position determination technique using a satellite positioning system based on whether the location related data indicates that the remote mobile device is inside of a building and outside of the building.

40. The apparatus of claim 39, wherein the data related to the chemical characteristic of the environment comprises chemical sensor data, the processor being further configured to analyze the chemical sensor data to determine the chemical characteristic related.

41. The apparatus of claim 39, wherein the data related to the chemical characteristic of the environment comprises the chemical characteristic determined by the remote mobile device from chemical sensor data.

42. The apparatus of claim 39, wherein the processor is configured to determine the location related data for the remote mobile device based on the chemical characteristic by being configured to search the database for the location related data associated with the chemical characteristic of the environment.

43. An apparatus comprising:
means for receiving data from a remote mobile device related to a chemical characteristic of an environment in which the remote mobile device is present;
means for determining location related data for the remote mobile device based on the chemical characteristic and a database that stores chemical characteristics associated with location related data, wherein the location related data comprises a general or specific location of the remote mobile device or assistance data for the remote mobile device to determine its location;

means for transmitting the location related data to the remote mobile device; and wherein the remote mobile device is controlled based on the location related data to switch the remote mobile device between a first position determination technique using terrestrial wireless signals and a second position determination technique using a satellite positioning system based on whether the location related data indicates that the remote mobile device is inside of a building and outside of the building.

44. The apparatus of claim 43, wherein the data related to the chemical characteristic of the environment comprises chemical sensor data, the apparatus further comprising means for analyzing the chemical sensor data to determine the chemical characteristic.

45. The apparatus of claim 43, wherein the data related to the chemical characteristic of the environment comprises the chemical characteristic determined by the remote mobile device from chemical sensor data.

46. The apparatus of claim 43, wherein the means for determining the location related data of the remote mobile device based on the chemical characteristic searches the database for the location related data associated with the chemical characteristic of the environment.

47. A non-transitory computer-readable medium including program code stored thereon, comprising:

program code to receive data from a remote mobile device related to a chemical characteristic of an environment in which the remote mobile device is present;

program code to determine location related data for the remote mobile device based on the chemical characteristic and a database that stores chemical characteristics associated with location related data, wherein the location related data comprises a general or specific location of the remote mobile device or assistance data for the remote mobile device to determine its location; and program code to transmit the location related data to the remote mobile device; and wherein the remote mobile device is controlled based on the location related data to switch the remote mobile device between a first position determination technique using terrestrial wireless signals and a second position determination technique using a satellite positioning system based on whether the location related data indicates that the remote mobile device is inside of a building and outside of the building.

48. The non-transitory computer-readable medium of claim 47, wherein the data related to the chemical characteristic of the environment comprises chemical sensor data, the non-transitory computer-readable medium further comprising program code to analyze the chemical sensor data to determine the chemical characteristic.

49. The non-transitory computer-readable medium of claim 47, wherein the data related to the chemical characteristic of the environment comprises the chemical characteristic determined by the remote mobile device from chemical sensor data.

50. The non-transitory computer-readable medium of claim 47, wherein the program code to determine the location related data of the remote mobile device based on the chemical characteristic comprises program code to search the database for the location related data associated with the chemical characteristic of the environment.

* * * * *